United States Patent [19]

Barrett

[11] 4,225,784

[45] Sep. 30, 1980

[54] COVALENTLY BOUND BIOLOGICAL SUBSTANCES TO PLASTIC MATERIALS AND USE IN RADIOASSAY

[75] Inventor: M. James Barrett, Saratoga, Calif.

[73] Assignee: Smith Kline Instruments, Inc., Philadelphia, Pa.

[21] Appl. No.: 696,959

[22] Filed: Jun. 17, 1976

Related U.S. Application Data

[63] Continuation-in-part of Ser. No. 511,952, Oct. 4, 1974, Pat. No. 4,001,583.

[51] Int. Cl.² ............................................. G01T 1/161
[52] U.S. Cl. ....................................... 250/303; 424/1; 424/12
[58] Field of Search ..................... 250/303; 424/1.0, 8, 424/12

[56] References Cited

U.S. PATENT DOCUMENTS

| | | | |
|---|---|---|---|
| 3,414,383 | 12/1968 | Murphy | 424/1 |
| 3,505,019 | 4/1970 | Axen et al. | 424/1 |
| 3,645,852 | 2/1972 | Axen et al. | 424/1 |
| 3,646,346 | 2/1972 | Catt | 250/303 |
| 3,666,854 | 5/1972 | Eisentraut | 424/1 |
| 3,826,619 | 7/1974 | Bratv | 424/1 |
| 3,836,433 | 9/1974 | Wirth et al. | 424/12 |
| 3,941,876 | 3/1976 | Marinkovich | 424/1 |
| 3,949,064 | 4/1976 | Bornstein et al. | 424/1 |
| 3,951,748 | 4/1976 | Devlin et al. | 424/12 |

FOREIGN PATENT DOCUMENTS 1257263 12/1971 United Kingdom ..................... 424/12

OTHER PUBLICATIONS

Principles of Competitive Protein Binding Assays, by Odell et al., pp. 312–315.

Primary Examiner—Harold A. Dixon
Attorney, Agent, or Firm—Richard D. Foggio

[57] ABSTRACT

Covalently bound biological substances to plastic materials whose inside surfaces have been coated with glutaraldehyde, with or without prior treatment with an aliphatic amine or diamine, useful in radioimmunoassay procedures.

2 Claims, No Drawings

COVALENTLY BOUND BIOLOGICAL SUBSTANCES TO PLASTIC MATERIALS AND USE IN RADIOASSAY

This application is a continuation-in-part of application Ser. No. 511,952 filed Oct. 4, 1974, now U.S. Pat. No. 4,001,583.

This invention relates to a method of covalently binding substances to plastic materials and to immunological determinations employing such bound substances.

In radioimmunoassay or competitive protein binding radioassay, the compound to be measured, generally the antigen, is allowed to compete with a similar or a chemically related radioactive compound for a limited number of binding sites on the antibodies or on the specific binding proteins. The antibody bound radioactive labeled compound is then separated form the free labeled compound and measured. Separation methods currently used, for example, electrophoresis, gel filtration, precipitation of free antigen with charcoal and precipitation of bound antigen with salt or another antibody, are often time consuming, complicated and do not give clear cut separation. Fixation of antibodies to the wall of a test tube enables the separation of the bound and free antigen by simple decantation.

It is an object of this invention to provide covalently bound substances to plastic materials which are useful in radioimmunoassays.

It is a further object of this invention to provide a method of covalently binding substances to plastic materials.

It is another object of this invention to provide a method of radioassaying for biological substances which includes using covalently bound immunological counterparts, such as antibodies.

It is an additional object to provide a radioassay material comprised of covalently bound substances to plastic materials.

These and other related objects are achieved as follows. Antibodies, specific binding proteins or other protein material such as enzymes are covalently linked through their amino and other reactive groups to active aldehyde groups of aliphatic dialdehydes, such as glutaraldehyde, that have been previously polymerized on the inside surface of a plastic material, such as a plastic test tube, for example a polypropylene or a polyethylene test tube.

The polymerized glutaraldehyde may in turn be attached to aliphatic primary amines of the general formula $CH_3\text{-}(CH_2)_n\text{-}NH_2$ where n is an integer of from 5 to 20, preferably 18, or aliphatic diamines of the general formula $CH_3\text{-}(CH_2)_n\text{-}NH\text{-}(CH_2)_m\text{-}NH_2$ where n and m are integers of from 3 to 20, preferably where n is 18 and m is 3. In this embodiment of the invention, prior to reaction with glutaraldehyde the plastic material is heated in a solution of the amine or diamine (as defined above) at temperatures above 50° C., preferably at 90° C. The excess amine or diamine is washed away and the plastic is treated with a solution of glutaraldehyde at room temperature, or a slightly elevated temperature, for example at 56° C. for a period of time extending from 1 to 2 hours to 1 to 2 days. Thus it is within the scope of the method of this invention that glutaraldehyde is polymerized directly on the inside surface of a plastic material such as a plastic test tube with or without prior treatment with an aliphatic amine or diamine.

In order to carry out a radioassay a mixture containing buffer, labeled antigen or analogues and unlabeled antigen or analogues from a biological fluid, such as serum, or from a standard solution is incubated in a plastic test tube with antibody or other specific binding protein covalently bound to the inside surface of the test tube according to the method of this invention. After a suitable incubation period the free antigen is removed rapidly and simply by decantation, leaving no time for readjustment of the established equilibrium. The radioactive antigen bound to the test tube is counted after the tube has been rinsed with buffer. The entire procedure is simple, rapid and no special skill is required.

It is believed that there is a self-polymerization of the aldehyde material on the surface of the plastic followed by a Schiff base-type coupling of the protein to the active aldehyde group.

The term "immunological counterpart" used herein denotes either an antigen or an antibody which reacts specifically with the corresponding antibody or antigen. The term "biological substance" used herein denotes a material of biological origin such as an antigen, antibody or enzyme, all of which being capable of chemically reacting with an aldehyde group. Unreacted amino groups present in the protein chains of most biological substances provide such chemically reactive groups.

TREATMENT OF PLASTIC TUBES

An aqueous solution of glutaraldehyde is dispensed into a plastic test tube, for example a polypropylene or polyethylene test tube, and is allowed to remain in contact with the inner surface of the test tube at room temperature or slightly elevated temperature, for example 56° C., for a period of time such as 1 to 2 hours to 1 to 2 days. The glutaraldehyde polymerizes on the surface of the plastic and forms a thin layer of polymer on the inner surface of the plastic test tube with a large number of active aldehyde groups that can react covalently with primary amino groups of antibodies or proteins.

The polymerization of glutaraldehyde occurs at a wide pH range, namely from 3 to 10. Also, the glutaraldehyde solution polymerizes on plastic surfaces over a wide range of aldehyde concentration, namely 0.1, 0.2, 0.5, 1 or 2% glutaraldehyde. The amount of glutaraldehyde polymer and consequently the number of active aldehyde groups on the plastic surface can be increased or decreased by varying the concentration of the aldehyde solution, incubation time and temperature. Excess active aldehyde groups on the plastic surface that are not used up in consequent protein coupling can be blocked by reacting with compounds having primary amino groups such as monoethanolamine or lysine.

After the glutaraldehyde is polymerized on the surface of the test tube, the aldehyde solution is removed by aspiration and the tube is washed thoroughly with deionized water. Tubes thus prepared are ready for use in a radioassay comprising protein or antibody coupling. The aldehyde treated tubes are very stable and retain their ability to couple protein even after washings with concentreated salt solutions and detergents.

COVALENT COUPLING WITH TREATED TUBES

Antibodies and proteins are coupled to the active aldehyde groups on the glutaraldehyde treated test tube surface through their primary amino groups. The rate and the amount of protein coupled to the test tubes is directly proportional to the concentration of the protein solution used. However, the maximum amount of protein that can be coupled to the surface is governed by the size of the protein molecule and the area of the plastic surface. Using $I^{125}$-gamma globulin ($\gamma G$), molecular weight 170,000, as a model protein, experimental data indicates that approximately 1.2 $\mu$g of $\gamma G$ is the maximum amount that can be coupled to 1 sq. cm. of a glutaraldehyde treated plastic surface. This amount is approximately equal to the calculated theoretical mass of gamma globulin that is required to form a monolayer of gamma globulin over the glutaraldehyde treated plastic surface. The $\gamma G$ molecule is an ellipse with diameters of 44A and 235A. If the $\gamma G$ molecule is coupled to the glutaraldehyde treated plastic surface along its short axis, then, the mass of $\gamma G$ required to form a monolayer of 1 sq. cm. surface area will be:

$$\frac{1 \text{ sq. cm.}}{44 \times 44 \times 10^{-6} \text{ sq. cm.}} \times \frac{1}{6.023 \times 10^{23}} \times 170,000 \text{ gm} = 1.5 \ \mu g \ \gamma G$$

An antibody solution of from 1 to 100 $\mu$g of protein per ml of buffer is dispensed into a glutaraldehyde treated tube and allowed to remain in contact with the treated surface at 4° C. for 15 hours. The antibody solution is removed by aspiration and, after rinsing the tube thoroughly with buffer, it can be used immediately for radioimmunoassay or stored for months until use. The antibody coated tubes are excellent for radioimmunoassay to give reproducible results, because (1) the antibody covalently coupled to the test tube is very stable and cannot be washed away (2) the antibodies so coupled to the wall retain their immunological reactivity for a long period of time and (3) a quantitated and precise amount of antibody can be coupled to each tube by controling the concentration of the coupling solution. The following experiment is illustrative.

(A) 2 ml of 0.1% glutaraldehyde in 0.1 M carbonate buffer, pH 9.0 is dispensed into each of 50 polypropylene tubes measuring 1.1×5.5 cm. The tubes are incubated at 56° C. for 3 hours, cooled at room temperature, and the aldehyde solution removed by aspiration. The tubes are washed 10× with deionized water.

(B) An $I^{125}$ labeled human gamma globulin solution at 15 $\mu$g protein per ml of 0.1 M phosphate buffer pH 7.0 is prepared and 2 ml of the human gamma globulin (HGG) solution is dispensed into each glutaraldehyde treated tube. The amount of $I^{125}$ HGG dispensed into each tube is counted (79,398±514 cpm). The $I^{125}$ HGG solution is left inside the tube at 4° C. for 15 hours. After the incubation period, the $I^{125}$ HGG solution is removed by aspiration. The $I^{125}$ HGG bound to the wall is counted after the tubes have been thoroughly rinsed. The amount of $I^{125}$ HGG coupled to the wall has a mean of 3.013 $\mu$g±0.067 $\mu$g (represented by 7975±178 cpm) a coefficient of variance of 2.24. The $I^{125}$ HGG coupled to the aldehyde treated surface cannot be washed away with 1% S.D.S. (sodium lauryl sulfate or dodecyl sodium sulfate). The $I^{125}$ HGG absorbed nonspecifically to plastic surfaces that have not been treated with glutaraldehyde, however, can be removed by washing with 1% S.D.S. The $I^{125}$ HGG coated tubes are stored at 4° C. with 3 ml of 0.1 M phosphate buffer in the tubes. The tubes are taken out at weekly intervals, shaken, and the amount of $I^{125}$ HGG remaining coupled to the tubes is re-determined. No appreciable decrease in the amount of $I^{125}$ HGG coupled to the wall is observed after a period of 6 or more months.

The following example illustrates the use of the present invention as applied in the radioimmunoassay of thyroxine in serum. This example is to be construed as merely illustrative, and not limitative in any way whatsoever. Besides antibodies, specific binding proteins such as intrinsic factor for Vitamin $B_{12}$ assay and $\beta$-Lactoglobulin in Folic Acid assay, can all be covalently coupled to glutaraldehyde treated tubes. In other examples, even the antigen, for example thyroxine, can be covalently coupled to the test tube and used for the determination of thyroxine-binding globulin in serum.

EXAMPLE 1

(A) 2 ml of 0.1% glutaraldehyde in 0.100 M carbonate buffer, pH 9.0 is dispensed into each of the 1.1×5.5 cm polypropylene tubes, incubated at 56° C. for 2 hours, cooled to room temperature and the aldehyde solution is removed by aspiration. The aldehyde treated tubes are washed 10× with deionized water.

(B) Antiserum to thyroxine is obtained by immunizing rabbits with $T_4$-Bovine Serum Albumin conjugate. The antibody to $T_4$-Bovine Serum Albumin is obtained by running the antiserum through a diethylaminoethyl cellulose column equilibrated with 0.01 phosphate buffer pH 6.8. The gamma globulin fraction containing $T_4$-antibodies are collected, protein concentration is determined by the Lowry method (O. H. Lowry, N. J. Rosebrough, A. L. Farr, and R. J. Randall, "Protein Measurement with the Folin Phenol Reagent." *J. Biol. Chem.*, 193, 265 (1951) and the fractions diluted to 15 $\mu$g per ml of 0.1 M phosphate buffer pH 7.0.

(C) 2 ml of the antibody solution is dispensed into each of the glutaraldehyde treated tubes, allowed to remain at 4° C. overnight, decanted, rinsed 1× with 0.1 M phosphate buffer, pH 7.0; 1× with 0.9% sodium chloride with 1% Bovine Serum Albumin, pH 7.0; 1× with 0.05 M phosphate buffer, pH 7.4 with 0.05% sodium azide, 0.9% sodium chloride, 0.3% bovine serum albumin and 0.05% Tween 20. All treated vials are air dried.

(d) Thyroxine Assay (1) Pipette 20λ of serum samples and standards at 0, 2.5, 5, 10, 20 $\mu$g% range into appropriately labeled $T_4$-antibody coated vials.

(2) Dispense into each vial 2 ml of 0.1 M Tris-Maleate buffer, pH 8.2±0.2 containing 300 $\mu$g of 8-anilinonaphthalene-sulfonic acid, sodium salt; 200 $\mu$g of sodium salicylate and 0.5 ng radioactive $T_4^{125}I$ with approximately 39,500 cpm.

(3) Vortex mix. Incubate at room temperature for 60 minutes.

(4) Decant, removing the last drop of reaction mixture by inverting the vials over a paper towel.

(5) Count all the vials in a gamma counter.

(E) Results (1) Compute $B/B_o$ as follows:

$$\frac{\text{net counts of standards or samples}}{\text{net counts of zero standard}} \times 100\%$$

(2) Construct $T_4$ standard curve and determine the values of the "unknowns" in $\mu$g% from the standard curve as in the following example:

| Tube | Net cpm | cpm | % Bound | Average % Bound | Value $T_4$ in µg % |
|---|---|---|---|---|---|
| Machine | 138 | — | — | — | — |
| Background | 139 | | | | |
| 0 µg $T_4$ | 12096 | 11958 | | 100% | |
| Standard | 11643 | 11505 | | | |
| 2.5 µg % $T_4$ | 9258 | 9120 | 77.7 | | |
| Standard | 9219 | 9081 | 77.4 | 77.6% | |
| 5.0 µg % $T_4$ | 7511 | 7373 | 62.8 | | |
| Standard | 7347 | 7209 | 61.5 | 62.2% | |
| 10.0 µg % $T_4$ | 5652 | 5514 | 47.0 | | |
| Standard | 5806 | 5668 | 48.3 | 47.7% | |
| 20.0 µg % $T_4$ | 4152 | 4014 | 34.2 | | |
| Standard | 3986 | 3848 | 32.8 | 33.5% | |
| Unknown #1 | 6931 | 6793 | 57.9 | | |
| | 6902 | 6764 | 57.7 | 57.8% | 6.2 µg % |
| Unknown #2 | 5052 | 4883 | 41.6 | | |
| | 4857 | 4719 | 40.2 | 40.9% | 14.0 µg % |

(F) A 10% decrease in protein concentration is observed after the $T_4$ antibody solution is used once to coat glutaraldehyde treated tubes. This $T_4$ antibody solution can be reused for coating tubes after the concentration of the $T_4$ antibody solution is re-adjusted to 15 µg protein per ml.

EXAMPLE 2

DETERMINATION OF VITAMIN $B_{12}$ IN SERUM (A) Preparation of Intrinsic Factor coated tube (1) 4 ml of 8 mM octadecylamine in 0.1 M sodium acetate buffer pH 5.0 is dispensed into each of the 1.1×5.5 cm polypropylene tubes, incubated at 97° C. for 2 hours, cooled to room temperature, octadecylamine solutin decanted out, and the tubes washed 10× with deionized water (2) 4 ml of 2% glutaraldehyde in 0.1 M carbonate buffer, pH 9.0 is dispensed into each of the amine treated tubes, incubated at 56° C. for 2 hours, cooled to room temprature and aldehyde solution removed by aspiration. The amine and aldehyde treated tubes are washed 10× with deionized water.

(3) 3 ml of intrinsic factor at 100 µg protein per ml of 0.1 M phosphate buffer pH 6.0 is dispensed into each of the amine and aldehyde treated tubes, allowed to remain at 4° C. overnight, the intrinsic factor solution decanted out and the coated tube washed 10× with deionized water.

(B) $B_{12}$ Assay (1) dispense 3 ml assay buffer into each intrinsic factor coated tube: 0.04 M glutamate pH 4.0 with 4 µg of cyanide per ml.

(2) add 100λ $B_{12}$ standard containing 0, 20, 40, 80, 160, 320 and 650 picograms (pg) of $B_{12}$ (3) add 50λ $Co^{57}$-$B_{12}$ containing 20 pg of $Co^{57}$-$B_{12}$ with 38,000 cpm (4) vortex and allow to remain at room temperature for 1 hour (5) decant, rinse tube 2× with assay buffer, count.

(C) Results

| $B_{12}$ Standard (pg) added in 100λ volume | $Co^{57}$—$B_{12}$(cpm) Bound to tube | $B/B_o \times 100$ |
|---|---|---|
| 0 | 1057 | 100% |
| 0 | 891 | |
| 20 | 835 | 84.9% |
| 20 | 860 | |
| 40 | 843 | 82.1% |
| 40 | 805 | |
| 80 | 660 | 70.1% |
| 80 | 788 | |
| 160 | 544 | 52.1% |
| 160 | 601 | |
| 320 | 457 | 39.1% |
| 320 | 472 | |
| 640 | 390 | 30.9% |
| 640 | 402 | |
| Background | 138 | |

For convenience, the aldehyde treated plastic tubes prepared in accordance with this invention are made avalable in an assay kit, for example as follows:

ABBREVIATED $T_4$-DIAGNOSTIC TEST (25 TESTS)

(A) $T_4$ Test Kit Contents (Store at 2°–5° C.)

(1) 25 Immunotubes—with $T_4$ antibody (rabbit) covalently coupled to the inside of the tubes (2) 5 vials of standard serum—(human) 0.5 ml vials at 0, 2.5, 5.0, 10.0, 20.0 µg/100 ml L-thyroxine (human serum containing sodium azide)

(3) 1 vial assay buffer—when dissolved in 55 ml $H_2O$ concentrations are: 0.1 M 2-amino-2-hydroxymethyl-1,3-propanediol (TRIS), 0.025 M maleic acid, 0.62 mM sodium silicylate, 0.47 mM 8-anilino-1-naphthalene sulfonic acid (ANS)

(4) 1 vial—$T_4I^{125}$ (Thyroxine—$I^{125}$) contains less than 1.0 microCuries.

(B) Procedures (1) Allow all reagents and serum samples to equilibrate at room temperature before use. Carry all procedures at room temperature.

(2) Dissolve the contents of the vial labelle ANS-Salicylate Buffer in 55 ml deionized $H_2O$.

(3) Transfer the radioactive $T_4I^{125}$ solution into the ANS-Salicylate Buffer vial by rinsing the vial labelled $T_4I^{125}$ Solution with ANS-Salicylate Buffer twice.

(4) Pipette 20 µl of serum samples and standards into appropriately labelled $T_4$-Antibody coated immunotubes.

(5) Dispense with an automatic pipettor 2 ml of $T_4I^{125}$-ANS-Salicylate buffer mixture into each of the reaction vials.

(6) Vortex mix. Incubate at room temperature for 60 minutes.

(7) Decant and discard the reaction mixture, removing the last drop of liquid by inverting the vials over a paper towel.

(8) Count all the vials in a gamma counter.

(9) Compute $B/B_0$ as follows:

$$\frac{\text{net counts of standards or samples}}{\text{net counts of zero standard}} \times 100\%$$

(10) Construct $T_4$ standard curve and determine the values of the "unknowns" in µg% from the standard curve.

U.S. Pat. No. 3,634,123 discloses a method of treating a plastic surface to retard coagulation of blood which comprises treating the surface with a cationic surface-active agent and then further treating with an anticoagulant such as heparin. The method requires that the protein substance (heparin) have a net negative charge at the same pH that the cationic surface-active agent (amine) is positively charged. Lagergren, H. R. and Eriksson, J. C., Trans. Amer. Soc. Int. Organs, 17:10 (1971), disclose the improvement of immersing a heparinized plastic polymer surface in a 1% glutaraldehyde solution thereby cross-linking the heparin molecules. The aldehyde, however, is introduced after the protein has been absorbed ionically to the surface.

U.S. Pat. No. 3,553,310 discloses a method of coating carrier particles having proteinaceous surfaces with an aldehyde material which are then useful for immunological testing.

U.S. Pat. No. 3,646,346 discloses a method of adsorbing on the surface of a test tube an antibody and subsequent use of the coated tube in a radioimmunoassay. The antibody is adsorbed directly to the surface of the tube.

British Pat. No. 1,257,263 discloses a method of forming covalently bonded bridges between protein molecules with or without formation of such bridges between the substrate and protein substance. The stabilized proteins are not contemplated for use in radioimmunoassay. There is no disclosure of coating a substrate surface with an aldehyde material prior to introduction of a protein substance.

Prior art disclosures thus include the binding of heparin to polypropylene tubes previously treated with aliphatic diamines, followed by surface treatment with glutaraldehyde, the cross-linking of proteins with glutaraldehyde for use in the preparation of immunoadsorbents, and the use of antibody-coated plastic tubes without aldehyde pretreatment in radioimmunoassay. There is no report of the use of plastic tubes, coated with polymerized glutaraldehyde with or without aliphatic amine polymers prior to application of antibody, in radioimmunoassay procedures.

It is an additional object of this invention to provide a method of determining the degree of unsaturation of carriers of biologically active compounds in biological fluids. For example, to measure unsaturated binding capacity of hormone binding globulin and other proteins. In one aspect, this invention relates to an improved method for removing free thyroid hormones from mixtures containing hormones in a free state and hormones which are bound to hormone binding globulin and other proteins.

Various diagnostic tests are known in the art for determining thyroid function. These tests include the basal metabolism test, the thyroid uptake test and various colorimetric and chemical procedures for determining the level of thyroxine iodine in the blood. Among the most accurate tests available are the diagnostic tests which utilize radioisotope labeled hormone to indirectly determine the level of thyroid hormones, thyroxine and triiodothyronine present in body fluids. Specifically, these tests include a test commonly referred to as the T-3 uptake test which measures the unsaturated binding capacity of thyrobinding globulin and other proteins within a body fluid such as blood.

T-3 uptake tests include the steps of adding the radioisotope labeled hormone to a solution containing a sample of hormone produced within the body and thyrobinding globulin (TBG), separating the resulting thyrobinding globulin containing bound hormone from the resulting unbound hormone, and counting the radioactivity of either the bound or unbound hormone. This counting procedure will indirectly indicate the amount of endogenous hormone which is bound to the natural globulin and protein binding sites within the blood.

Thus, the T-3 uptake test depends for its accuracy upon the efficient separation between the bound and unbound thyroid hormone in the test sample. The currently available methods for removal of these hormones include ion exchange resins such as the ion exchangers having strongly basic amino or quaternary ammonium groups as disclosed in U.S. Pat. No. 3,414,383. These organic ion exchange resins can be either in loose forms, or incorporated in polyurethane sponges as disclosed in U.S. Pat. No. 3,206,602, or enclosed in porous bags or the like. Another available method involves a selective absorption of the free hormones by inorganic silicates as revealed in U.S. Pat. No. 3,666,854.

The major disadvantages of the currently available separation methods described above are:

(a) They require manual addition of bound-free separating agents such as silicate tablets, resin sponges, or charcoal.

(b) Final values are time and temperature dependent.

(c) They require wash steps.

(d) They require centrifugation or use of columns as supports.

As a result of (a), (b), (c) and (d) present systems are not readily automatable.

Therefore, one object of this invention is to provide an improved diagnostic test for indirectly determining the level of thyroid hormone in a body fluid by detecting the degree of unsaturation of thyrobinding globulin (TBG).

Another object of this invention is to provide an improved method of separating thyroid hormone bound to thyroidbinding globulin and other proteins from unbound thyroid hormones.

According to the invention, the separation of the free hormones from hormones bound to natural binding sites (thyrobinding globulin and other proteins) in a diagnostic test is carried out by attachment of the free hormones to hormone specific protein immobilized on insoluble supports and results in a highly efficient, simple, fast and reproducible result. This separation is conducted by aspiration or decantation. Either the supernatant fluid or the immobilized hormone specific protein can be counted in a scintillation well counter; however, it is preferred that the immobilized hormone specific protein be counted.

The particularly novel aspect of this invention is the use of an antibody (hormone specific protein) for determining the degree of unsaturation of a carrier of a biologically active compound in a biological fluid. For this purpose the antibody can be immobilized on any art-recognized support means. Such support means would include, for example, adsorbtion to the walls of a plastic test tube, ion exchange chromatography resin, precipitation with polyethylene glycol, a second antibody or ammonium sulfate, and a gel sieve. A useful support means, as described more fully hereinbefore, is the wall of a plastic test tube treated with glutaraldehyde to which is coupled the antibody.

In operation, immobilized hormone specific protein is exposed to patient sample in a buffer containing radioactively labeled hormone. For example, a hormone specific protein such as anti-triiodothyronine gamma globulin, can be coupled to the walls of a glutaraldehyde treated plastic test tube. Patient sample, preferably serum, is added to the tube followed by a buffer containing radioactively labeled hormone such as triiodothyronine. The solution is mixed for 5 seconds followed by incubation for at least 15 minutes, but preferably 1 hour. During the incubation, competition for T-3 $I^{125}$ occurs between unsaturated binding sites on the thyrobinding globulin and hormone specific protein. At any time thereafter, the buffer is removed from the tube, and the tube or buffer, but preferably tube, is counted. The procedure can occur at any convenient temperature, for example, room temperature. Additionally, the period of contact between the immobilized hormone specific protein and test sample is not critical past 15 minutes after the mixing.

This invention basically constitutes an improved diagnostic test which measures indirectly thyroid hormones by determining the unsaturated binding capacity of the thyrobinding globulin and other proteins within body fluids by use of immobilized hormone specific protein. The body fluid being assayed is normally serum, but unsaturated binding capacity of thyrobinding globulin can be determined in blood plasma. The basic improved test of this invention is described as follows:

TEST FOR UNSATURATED BINDING CAPACITY OF THYROBINDING GLOBULIN AND OTHER PROTEINS

In this test, a tracer quantity of radioactive isotope labeled hormone is admixed with a known amount of body fluid (serum) in a plastic tube to the walls of which hormone specific protein is coupled, thoroughly mixed, then separated therefrom by aspiration or decantation. No centrifugation or wash steps are required. At this point either the resulting supernatant fluid from the test solution or the tube can be counted in a scintillation wall counter to determine the amount of radioactive isotope labeled hormone therein. This determination will indirectly show the level of hormone which was originally bound to the binding sites of thyrobinding globulin and other proteins within the serum. A preferred method is as follows:

0.02 milliliter of the sample serum (from the patient) is added to the tube. It is noted that various volumes of the serum can be employed, but this amount is preferred in that it yields the greatest difference between normal and abnormal sera that permits a substantial amount of radioactivity to be bound to the immobilized hormone specific protein.

A tracer quantity of radioactive isotope labeled triiodothyronine or thyroxine, preferably triiodothyronine, in barbital buffer (diethyl barbituric acid pH 8.0, 0.050 M) is added. The hormone utilized is labeled with either radioactive $I^{131}$ or $I^{125}$ (or theoretically, any radioactive isotope of iodine, tritium, nitrogen or carbon). The $I^{125}$ is preferable because it has a half life of 60 days and it can be employed for at least 6 weeks; whereas, $I^{131}$ has a half life of 8 days and has a useful shelf life of about two weeks. It is noted that the barbital buffer could be employed with an alternate pH and molarity and other buffers could be used. For example, the barbital buffer can be used in a pH range of from 6.8 to 8.8 and other buffers such as tris(hydroxymethyl)aminomethane, tris(hydroxymethyl)aminomethane-maleate, sodium phosphate, and potassium phosphate can be used.

At any convenient time, for example, between 15 minutes and 4 hours after mixing, the sample solution is decanted or aspirated to separate patient's sample bound radioactive hormone from immobilized hormone specific protein. At this point, either the discarded supernatant fluid or the immobilized hormone specific protein can be counted in the scintillation well counter. However, it is preferred that the immobilized hormone specific protein be counted. The percent free radioactive hormone is determined by recording the counts attached to the immobilized hormone specific protein and comparing them to a serum standardized with an inorganic silicate or ion exchange resin.

The normal range employing the above described method standardized by silicates is 34–48 percent. The normal range employing the above described method standardized by ion exchange resin is 26–36 percent. Hypothyroidism and pregnancy yield values below the normal range while values in hyperthyroid patients are higher.

EXAMPLE 3

In this example, unsaturation of thyrobinding globulin was detected using anti-T-3 gamma globulin immobilized on the walls of polypropylene test tubes. The radioisotope ($I^{125}$) labeled hormone was triiodothyronine. Patient serum sample size was 0.02 milliliter and the buffer was 0.05 M barbital, pH 8.0. Serum samples from hypothyroid, normal and hyperthyroid patients were incubated for 60 minutes at room temperature. After the incubation, the buffer was aspirated and tubes counted. Comparison to counts obtained using a standardizing serum calibrated with an inorganic silicate gave the following results:

| | |
|---|---|
| Hypothyroid | 27% |
| Normal | 39.1% |
| Hyperthyroid | 55% |

The above results clearly indicate that use of anti-T-3 gamma globulin immobilized on the walls of an insoluble support, such as polypropylene test tubes is capable, in combination with T-3 $I^{125}$ in barbital buffer, of distinguishing between hypothyroid, normal and hyperthyroid patient samples.

EXAMPLE 4

In this example, unsaturation of thyrobinding globulin was detected using anti-thyroxine gamma globulin immobilized on the walls of polypropylene test tubes. The radioisotope ($I^{125}$) labeled hormone was thyroxine (T-4). Patient serum sample size was 0.02 milliliter and the buffer was 0.05 M barbital, pH 8.0. Serum samples from hypothyroid, normal and hyperthyroid patients were incubated for 60 minutes at room temperature. After the incubation, the buffer was aspirated and tubes counted. Comparison to counts obtained using a standardizing serum calibrated with an inorganic silicate gave the following results:

| | |
|---|---|
| Hypothyroid | 22 |
| Normal | 39 |
| Hyperthyroid | 62 |

The above results clearly indicate that use of anti-T-4 gamma globulin immobilized on the walls of an insoluble support, such as polypropylene test tubes is capable, in combination with T-4 $I^{125}$ in barbital buffer, of distinguishing between hypothyroid, normal and hyperthyroid patient samples.

EXAMPLE 5

The unsaturated binding capacity test as described in Example 3 and using triiodothyronine labeled with radioactive $I^{125}$ was conducted on three days by two technicians, three determinations on each sample. The following results were obtained:

| Sample 1 | | Sample 2 | |
|---|---|---|---|
| 42.9 | 48.1 | 41.4 | 43.7 |
| 44.3 | 46.7 | 42.8 | 41.4 |
| 44.7 | 46.7 | 41.8 | 43.1 |
| 43.0 | M = 44.09 | 39.4 | M = 41.10 |
|  | SD = 1.01 |  | SD = 1.00 |
| 43.6 | CV = 2.29 | 39.5 | CV = 2.4 |
| 43.6 |  | 41.1 |  |
| 44.1 |  | 40.7 |  |
| 43.9 |  | 41.1 |  |
| 43.6 |  | 40.5 |  |
| 43.7 |  | 40.9 |  |
| 43.9 |  | 42.9 |  |
| 45.4 |  | 41.3 |  |
| 43.7 |  | 41.2 |  |
| 44.7 |  | 40.8 |  |
| 43.4 |  | 41.9 |  |

The results indicated an extremely low coefficient of variation and that use of hormone specific protein, especially when immobilized, yields highly reproducible results.

EXAMPLE 6

The unsaturated binding capacity test as described in Example 3 was conducted on serum in the normal, hypothyroid and hyperthyroid except the quantity of patient serum, and quantity of anti-T-3 gamma globulin were varied.

| Serum Sample Size | Variation of Serum Sample Size Milliliters | | | | |
|---|---|---|---|---|---|
|  | .005 | .010 | .020 | .050 | 0.1 |
| Hypothyroid | 35 | 35.5 | 31.1 | 30.5 | 28.0 |
| Normal | 40.3 | 41.6 | 38.2 | 43.0 | 38.6 |
| Hyperthyroid | 48.8 | 52.5 | 56.0 | 64.0 | 64.5 |

Antibody Concentration

Antibody concentration is indicated by trace binding (same antibody serum pool used to make tubes. $T-3^{125}$ buffer used in assay was the same).

| Trace Binding | 19.8 | 12.5 |
|---|---|---|
| Hypothyroid | 28.2 | 26.4 |
| Normal | 38.8 | 38.8 |
| Hyperthyroid | 50.9 | 51.3 |

These results clearly indicate that the test system is capable of distinguishing between hypothyroid, normal and hyperthyroid patient sera using a broad range of serum sample sizes and different immobilized hormone specific antibody concentrations.

EXAMPLE 7

The unsaturated binding capacity test as described in Example 3 was conducted on sera in the normal, hypothyroid and hyperthyroid ranges with variation only in the incubation times.

|  | Time | | |
|---|---|---|---|
|  | 60 Minutes | 120 Minutes | 240 Minutes |
| Hypothyroid | 28.0 | 29.7 | 29.4 |
| Normal | 41 | 41 | 41 |
| Hyperthyroid | 44 | 44.7 | 44.5 |

This experiment clearly indicates that variation of incubation times do not affect significantly the final result obtained.

What is claimed is:

1. A method for indirectly determining the level of thyroid hormone in a biological fluid which comprises detecting the degree of unsaturation of thyrobinding globulin in said biological fluid by employing immobilized hormone specific protein.

2. The method of claim 1 wherein the hormone specific protein is anti-triiodothyronine gamma globulin.

* * * * *